United States Patent [19]

Lovalenti

[11] 4,385,233

[45] May 24, 1983

[54] FUSED GLASS DETECTOR

[75] Inventor: Sam Lovalenti, Toledo, Ohio

[73] Assignee: Owens-Illinois, Inc., Toledo, Ohio

[21] Appl. No.: 244,837

[22] Filed: Mar. 18, 1981

[51] Int. Cl.³ .............................................. G06M 7/00
[52] U.S. Cl. ................................ 250/223 B; 209/526; 356/240
[58] Field of Search ................... 250/223 B; 356/343, 356/240, 428, 435; 209/526

[56] References Cited

U.S. PATENT DOCUMENTS

| | | | |
|---|---|---|---|
| 3,245,529 | 4/1966 | Doud | 209/75 |
| 3,302,786 | 2/1967 | Conrad | 209/111.5 |
| 3,313,409 | 4/1967 | Johnson | 209/73 |
| 3,356,853 | 12/1967 | Rottmann | 250/223 |
| 3,745,314 | 7/1973 | Mathias et al. | 235/61.11 E |
| 4,225,035 | 9/1980 | Mohney et al. | 198/836 |
| 4,293,219 | 10/1981 | Ducloux | 356/240 |

*Primary Examiner*—David C. Nelms
*Assistant Examiner*—J. Brophy
*Attorney, Agent, or Firm*—D. T. Innis; M. E. Click; D. H. Wilson

[57] ABSTRACT

There is disclosed herein apparatus which views a glass container from above while the container is rotated about its vertical axis. A source of light, preferably a laser, has its beam swept diametrically back and forth across the bottom of the container to be examined. The inclusion of a piece of stuck or fused glass in the container will create a light output in the form of a pair of concentric halos of light above the container finish. The halos are sensed by two concentric arrays of solar cells positioned above the container. The output of the solar cells is fed to logic and reject electronics for selected rejection from a line of ware moving along a conveyor, depending upon whether or not the container has a piece of stuck glass therein. The apparatus and method of determining stuck glass is generally insensitive to mold numbers and other types of optical discontinuities that may be found in the container bottom because of the requirement that an output reject signal is obtained only when a plurality of solar cells are illuminated at the same time.

7 Claims, 5 Drawing Figures

FUSED GLASS DETECTOR

BACKGROUND OF THE INVENTION

This invention relates to inspecting glass containers for the specific defect or presence of "fused" or "stuck" particles of glass within the interior of the container and in particular, fused or stuck glass which is adhering to the interior bottom surface of the glass container.

In the manufacture of glassware, and in particular glass containers, occasionally a piece of glass which may originate at some other location within the glass plant, will find its way to the area where the containers are being either formed or handled after forming prior to being packed into shipping cartons. It should be understood that in almost any glass plant there is always the possibility that breakage will occur on the production line at various points along the line which might cause small pieces of glass to fly into or become enclosed in a newly formed glass container. When this occurs, at the time the glass is in a relatively hot state, it is very possible for the small piece of glass to become fused to the inner bottom surface of the glass container. It should be kept in mind that glass becomes soft and would fuse if the interfacial temperature were to approximate 800° between the glass particle and the interior bottom of the glass container. The container, after it is newly formed and set out on a dead plate or on the machine conveyor which moves the containers away from the forming machine, may have a sufficient temperature such that it will cause small particles of broken glass to adhere to the interior thereof. Thus, even if the containers, at some later time prior to packing, are swept with compressed air or are inverted, these small particles of glass will still adhere to the interior thereof.

It is desirable not to ship containers that might have stuck glass therein and for this reason, the present invention has as its principal object the selection and examination of glass containers, after they have been annealed, to determine the presence or absence of any fused glass that might be adhering to the interior thereof. While the invention may find its principal utility in determining fused or stuck glass in what are termed "wide mouth" containers, such as baby food jars, home canning jars, it will have equal utility when being used for inspecting tumblers or other hollow glass articles that can be illuminated from the bottom while being rotated about their vertical axis and positioned beneath an annular array of solar cells.

It has been known in the prior art to illuminate containers from below and to then examine the containers through the open upper mouth or finish area thereof. In most of these "prior art" types of inspection devices, it is important or necessary that the light source beneath the container be of a diffuse character so that mold marks or molded-in lettering which appears on the bottom of glass containers not give the appearance of a defect to the optical pick-up. Since most optical inspection apparatus for glass containers are looking for defects of the reflecting type, defects which will deflect (reflect or refract) light out of a projected direction, raised lettering will either make the image of the bottom of the bottle appear to have dark spots due to the reflection or refraction of the light.

It has also been the practice in the art to shine a light through the finish of the container and have it sweep the inner diameter of the bottom of the container, for example, as shown in U.S. Pat. No. 3,356,853. In this particular patent, however, the bottom wall of the hollow transparent container is being inspected for those types of defects that will cause a focused beam of light to be reflected or refracted out of the normal direction that it is taking from the source. It has also been known to inspect glass containers with the use of a laser beam as the light source and the light piping characteristics or internal reflections of the container wall have been utilized as a phenomenon in order to provide a means for illuminating reflecting type defects. Scanning the exterior of a laser illuminated sidewall of a container with a photo-sensitive pickup has been used to determine the reflectance of light out of the wall of the container due to a defect. Such defects are known as checks, stones or blisters appearing within the wall of the container. The use of a laser beam as a light source in the manner suggested above, may be found in U.S. Pat. No. 3,302,786 of common assignee with the present application.

SUMMARY OF THE INVENTION

This invention relates to apparatus for handling containers into and through an inspection position where the container is rotated about its vertical axis by engagement of the sidewall thereof by a drive wheel. A slotted dead plate, over which the rotating bottle is positioned, is illuminated by a laser beam which is being horizontally scanned through the slotted dead plate, thereby illuminating a diameter of the bottom of the container in a continuous scanning fashion. By having this arrangement, the full inner bottom wall of the container will be illuminated each revolution of the container. An array of solar cells positioned above the finish of the container in a circular pattern, of a diameter larger than the diameter of the container finish, will pick up light which is scattered or emanates from a piece of stuck glass within the interior bottom surface of the container, with the fused glass particle appearing as a point source of light radiating upwardly in all directions onto the solar cell array.

DETAILED DESCRIPTION OF THE DRAWINGS

Figure 1:
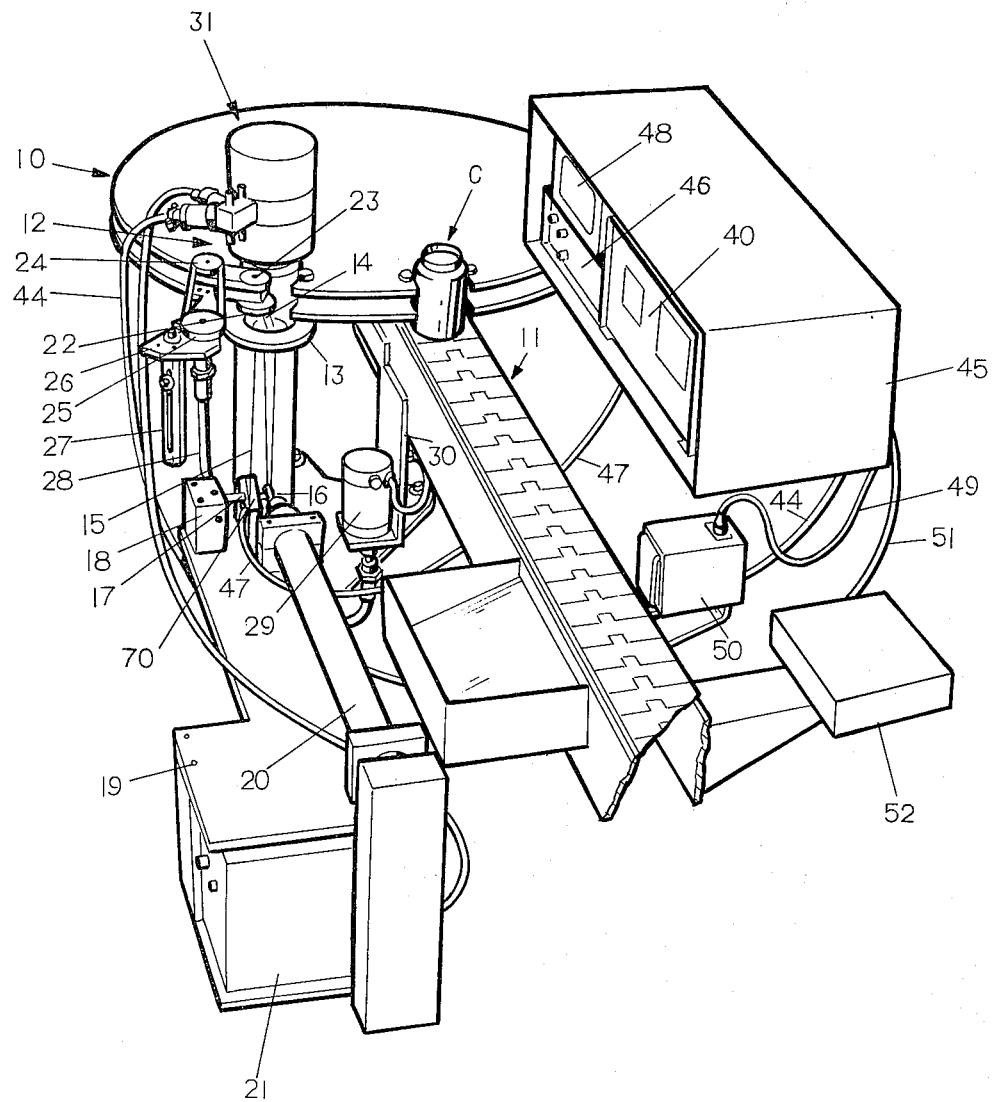
FIG. 1 is a schematic, perspective view of the apparatus of the invention.

With particular reference to FIG. 1 of the drawings, there is shown schematically a starwheel 10 of an automatic glassware inspection machine such as that shown in U.S. Pat. No. 3,313,409 to J. R. Johnson. It should be pointed out that the starwheel 10 only shows two pockets, one where the "stuck glass" detector of the present invention is positioned and a second pocket which is in alignment with a conveyor 11. In the actual embodiment of the invention, the starwheel 10 will have a plurality of pockets, usually eight in number, peripherally spaced about the circumference thereof and that an incoming conveyor will bring bottles into the starwheel at a position roughly 90° removed from the position shown as being in alignment with the conveyor 11, the 90° being in the counterclockwise direction as viewed in FIG. 1.

It should be pointed out that the starwheel 10 is indexed, since it has eight pockets through 45° angles and presents bottles, in series, to the inspection positions. The inspection position illustrated in FIG. 1 would correspond in the above-referred-to Johnson patent to the fifth and last inspection station just in advance of the exit or take-away conveyor. At the position designated 12, is a generally horizontal platform or dead plate 13 having an elongated, horizontal slot 14 formed therein. Beneath the plate 13, extends a vertical collimating tube 15. At the lower end of the collimating tube 15, is positioned an oscillating mirror 16. The mirror 16 is mounted on a horizontally extending shaft 17 which extends through the collimating tube 15. The outer end of the shaft 17 is carried within a housing 18 to secure the electro-optical scanner. A housing 70 holds the driver coils for driving the shaft 17 at a frequency of 2500 Hz. The housing 18 and the lower end of the collimating tube 15, are mounted on a generally horizontally extending support plate 19. The upper surface of the plate 19 may serve to support a laser 20 whose axis extends horizontally in the direction of and is aimed at the mirror 16. A suitable power supply 21 for the laser may be mounted beneath the plate 19.

With the mechanism just described, it can be seen that the laser beam, by striking the oscillating mirror 16, can be deflected through a fairly narrow included angle such that the beam coming therefrom will sweep back and forth across the length of the slot 14 in the plate 13. The plate 13 serves as the support for the container C which is to be examined. The container C is held and rotated within the confines of the starwheel by a side-engaging roller 22. The roller 22 is driven by an upper pulley 23 which in turn is driven by a belt extending over a second pulley 24, with the pulley 24 being belt driven by a drive pulley 25. The drive pulley 25 is mounted on a plate 26, which in turn is vertically adjustable relative to the starwheel supporting structure (not shown) by an adjustable bolt and slotted support member 27, as shown in FIG. 1. A more detailed description of a typical side-engaging, bottle rotation mechanism may be found in U.S. Pat. No. 4,225,035 assigned to the assignee of the present application. The driven pulley 25 is connected by a flexible cable 28 to a motor 29. The motor 29 is conveniently mounted on an angle bracket 30 which is connected to and supported from the side of the conveyor 11.

Figure 2:
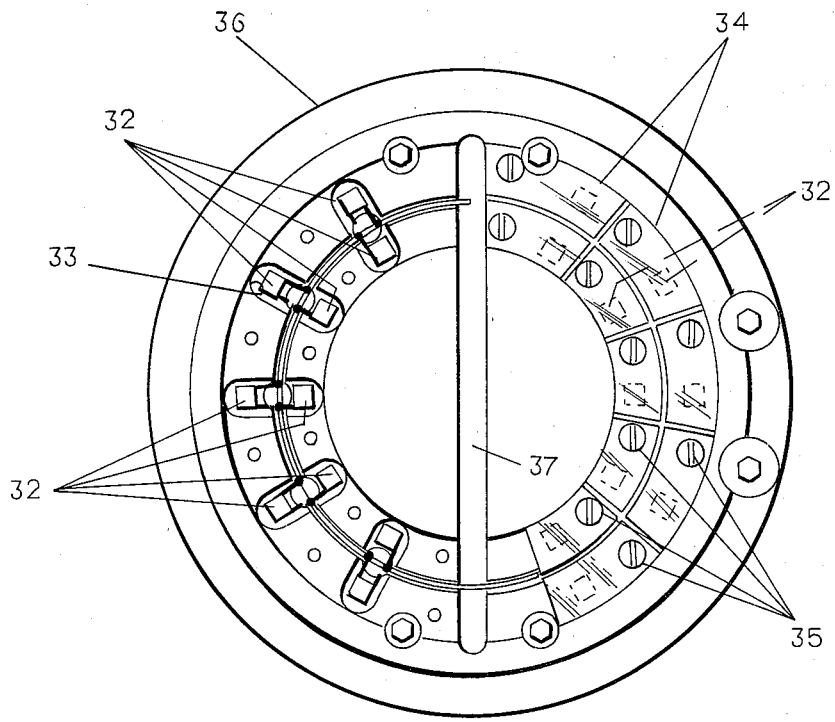
FIG. 2 is a plan view of the detector head assembly, showing the solar cell array of the invention.
Figure 3:
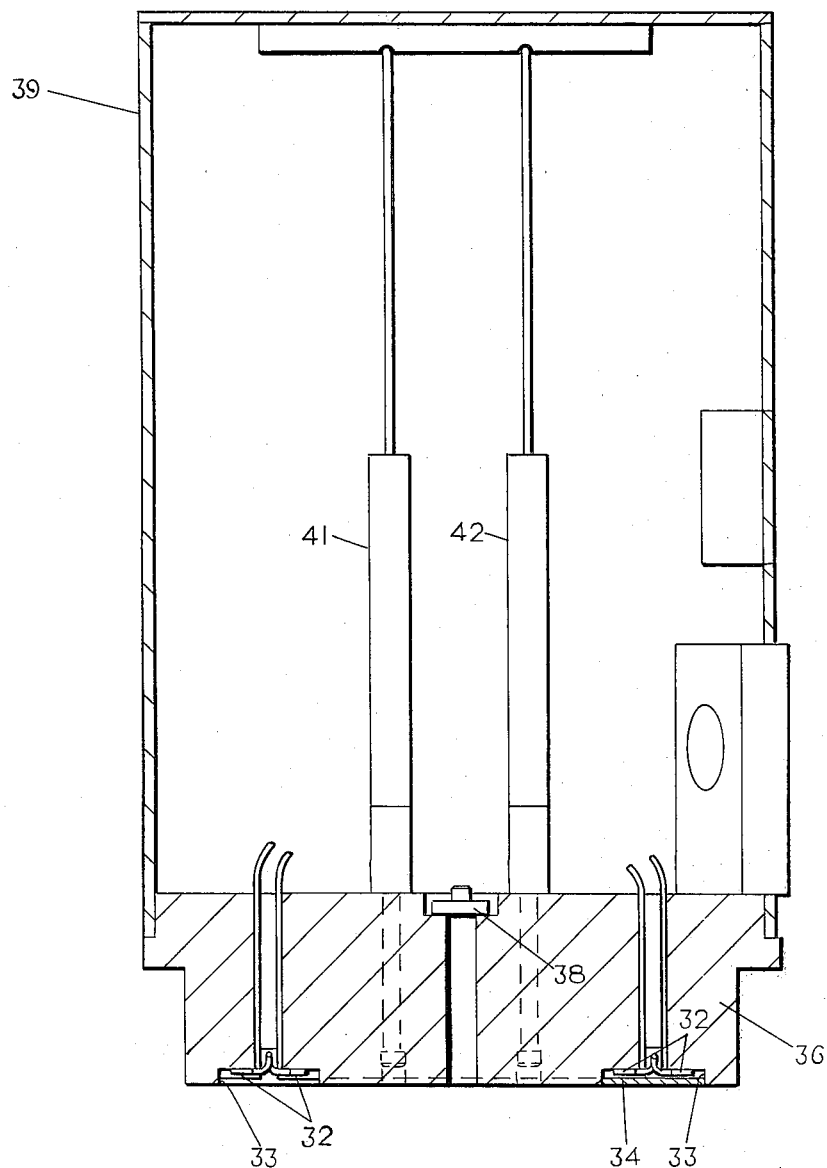
FIG. 3 is a cross-sectional view of the detector head assembly taken at line 3—3 of FIG. 2.

A gauge head housing, generally designated 31, is positioned coaxially above the container C, which is to be inspected and is shown in an enlarged view of greater detail in FIGS. 2 and 3. At the bottom of the gauging head housing will be found a circular array of solar cells, shown specifically in FIG. 2.

With reference to FIG. 2, it will be noted that, in the drawing, the left half of the array is shown without cover plates, while in the right half of the array the cells are shown with cover plates thereover. The solar cells 32 are actually positioned within recesses, as can best be seen in FIG. 3, the recesses being numbered 33.

In actual practice, the solar cells are cemented within the recesses in the manner illustrated, and then are provided with cover plates 34. The cover plates are held in position by screws 35, as shown in FIG. 2, it being understood that the cover plates and the screws 35 are threaded in a fairly thick block of material 36.

Diametrically across the center of the block 36, as shown in FIG. 3, is an elongated recess 37 which extends entirely through the thickness of the block. Overlying the recess 37 and above that surface which carries the solar cells is positioned a transparent, frosted plate 38. The plate 38 may have a horizontal line extending along the center of its length thereof, it being understood that when the laser system is being placed in operation and adjustment is being made of the position of the laser, as well as the position of the array of solar cells, that the laser light, as it sweeps through the slot 14 in the dead plate 13 it also will sweep back and forth in the recess 37 and the alignment of the recess relative to the slot 14 may be viewed by looking from above after the removal of a cover 39. As can readily be seen, viewing of the proper alignment of the sweeping laser beam relative to the detector head assembly is an important consideration, and will be more apparent as the operation of the invention is explained in greater detail hereinafter.

As can best be seen in FIG. 2, the solar cell arrays are in the form of two concentric circles with ten individual cells spaced circumferentially about the center of the array in each of the two coaxial arrays. It should be noted also that the cells are somewhat spaced from the illuminated diametrical area of the recess 37. Within the housing 39 will be carried preamplifiers for receiving the signals from the solar cells and amplifying these signals so that they may be transmitted to an electronic logic and reject interface cabinet designated 40. The preamplifiers are given reference numerals 41 and 42 in FIG. 3. As would be expected, the preamplifiers have their own printed circuit boards which have the required electronic components for effecting preamplification of the signals. It should be pointed out that the array of solar cells is summed and that when in operation, it is a combined signal from a greater number than three cells which could be used as a minimum number to indicate the presence of a piece of stuck glass. However, in most cases, it has been found that by requiring at least the output from the illumination of nine cells will give a more reliable and certain indication of the presence of fused glass within the interior of the container positioned over the slot 14.

Power to the gauge head may be by way of a cable 44 from the power supply in cabinet 40. The output from the preamplifiers will be fed through the cable 44 leading to the electronics cabinet 40. The cabinet 40, as shown in FIG. 1, is mounted in a console 45 that is conveniently placed for the operator to have easy access. In addition to the electronics cabinet, the console is provided with a scanner amplifier/power supply 46. The scanner amplifier/power supply 46 is connected by lead 47 to the mirror oscillator. A display device 48 may also be mounted within the console and when a reject interface 52 is connected to the stuck glass gauge output, along with the reject outputs of other inspection devices that would be incorporated with the other starwheel positioned mentioned above, it can provide a continuous display of the kinds of defects being detected and provide a count of them as well. The reject interface 52 is connected to the electronics display by cable 51. Further, the electronics 40 are provided with a connection 49 to a reject solenoid 50 mounted along the side of the conveyor 11 to thereby provide a signal to reject those containers which have been found to be defective.

It should also be apparent that one of the inspection positions to which the starwheel brings bottles may be, as taught in U.S. Pat. No. 4,745,314 to Mathias et al., a cavity identification reader, thus also providing information for display or print-out of the mold of origin of each defect detected, including the containers found to have stuck glass therein by the specifically disclosed apparatus.

Figure 4:
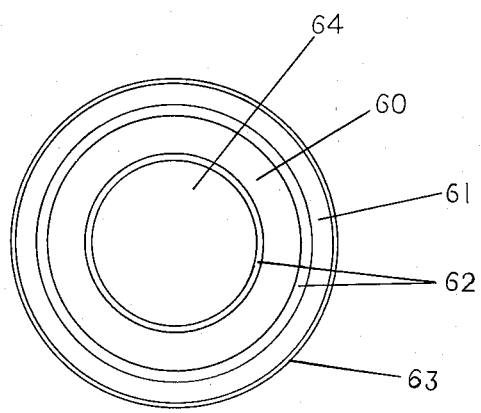
FIG. 4 is a top plan view of the light pattern emanating from the bottom of the container.

As stated before, and as illustrated in FIG. 4, the stuck glass that is lighted from below with the laser scan, appears to the observer as a point source of light which radiates in nearly all directions. As the light from the stuck glass radiates, it will be observed by a plurality of solar cells and, having selected a number whose combined outputs are greater than some minimum number, such as three, a lower threshold is established. It is necessary to pick a threshold because other defects may appear in the bottom of a container and act as a mirror or lens to either reflect or refract the light. The reflected or refracted light, however, is normally highly directional and would result in the illumination of perhaps one or two cells. Therefore, by choosing a larger number of cells as the level that will indicate stuck glass, the response will not be misleading. The other defects, such as checks, etc., are detectable by other devices that are positioned at the other stations of the inspection and gauging machine served by the starwheel.

Figure 5:
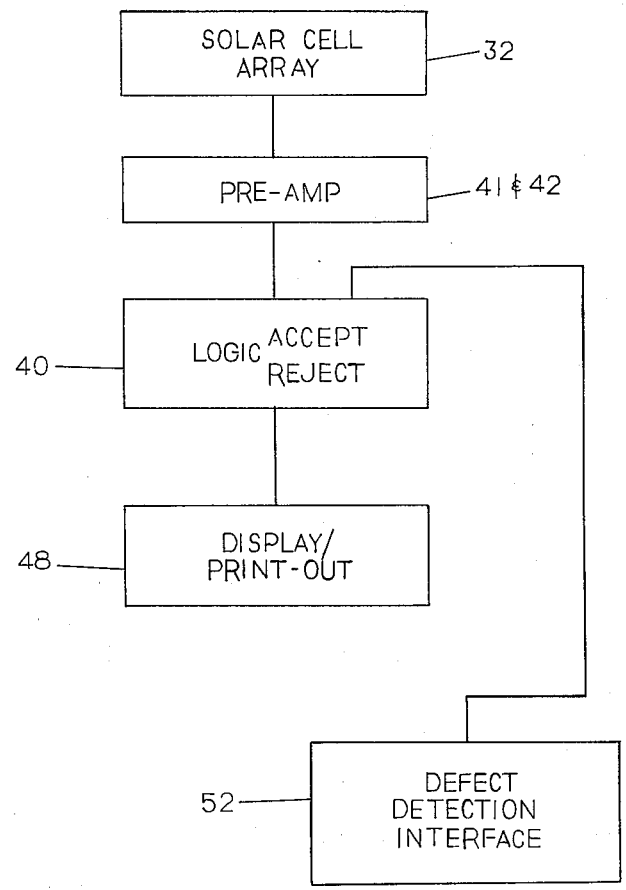
FIG. 5 is a schematic, diagrammatic view of a circuit diagram.

Reference to FIG. 5 may be had where a schematic circuit diagram is shown with the reference numerals applied thereto which correspond to those applied to the same parts found in FIGS. 1-3.

The array of photocells depicted in FIG. 2 may be correlated to the FIG. 4 view of the light pattern which is emanating from a piece of stuck glass found in the inner bottom wall of a baby food-size jar.

It should be kept in mind that FIG. 4 is what would be viewed or give the appearance of what is being seen if one were to place a piece of paper slightly above and spaced from the neck of a baby food jar and a piece of fused glass is illuminated.

There are two halos of light represented by two annular areas 60 and 61 on FIG. 4. Annular areas 62 appearing between the light areas 60, 61 and 64 appear as a relatively shaded area, as well as a shaded area 63 at the outer perimeter of the image. A center 64 of image may have a light area in the event the piece of stuck glass is within the direct view through the neck of the bottle. However, the array which is sensing light has no pickups within this viewing area; therefore, any light found in area 64 will have no effect on the sensitivity of this device. The two areas 60 and 61 correspond generally to the two arrays of solar cells, as shown in FIG. 2. The light which is emanating from a baby food container produces the two halos of light which are actually upwardly divergent from the shoulder and the finish or neck portion of the container respectively. The spacing of the array of photocells or the gauging head will be dependent upon the size of the container and the location of the image such as that shown in FIG. 4. By moving the head vertically relative to the finish of the container, the two halos of light will correspond to the two annular rings of the photocell arrays. It should be kept in mind that for different sizes of containers, the two halos will be of a different size, thus the vertical spacing between the lower end of the head and the bottle finish will be adjusted accordingly, so as to give the requisite alignment or coincidence.

I claim:

1. Apparatus for determining the presence of fused glass adhering to the interior bottom wall of a glass container comprising:
   a support plate having a horizontal, elongated slit formed therein;
   means for moving glass containers serially into position overlying the said support plate;
   means for rotating said container about its vertical axis;
   a source of light in the form of a beam;
   means scanning said beam back and forth along the length of said slit in said support plate;
   three or more individual solar cells in a generally circular array, said cells being positioned above and said array being coaxial with respect to the container which is in position over said supporting plate; and
   means connected to said solar cells for indicating when three or more of said solar cells are simultaneously illuminated.

2. The apparatus of claim 1 wherein said source of light is a laser beam.

3. The apparatus of claim 1 wherein said means scaning said beam comprises a mirror and means connected to said mirror for oscillating the mirror.

4. The apparatus of claim 1 wherein said container rotating means comprises a roller in engagement with the sidewall of said container and means for rotating said roller.

5. The apparatus of claim 1 further including means connecting said solar cells together as an annular array and output means electrically connected to the array of cells and responsive to illumination of three or more cells simultaneously.

6. The apparatus of claims 1 or 5 further including means connected to the output of said solar cell array and responsive to a signal therefrom for ejecting containers with stuck glass from a line thereof.

7. A method of inspecting glass containers for fused or stuck glass in the interior thereof comprising the steps of:
   moving the containers to be inspected into and out of an inspection station;
   rotating the container in station about its vertical axis;
   illuminating the bottom of the container by a narrow beam of light being moved back and forth across the diameter thereof;
   viewing the container from above with three or more solar cells in a horizontal, circular array; and
   indicating when three or more solar cells are simultaneously illuminated, as an indication of the presence of stuck or fused glass in the container.

* * * * *